US006518577B1

(12) United States Patent
Fang et al.

(10) Patent No.: US 6,518,577 B1
(45) Date of Patent: Feb. 11, 2003

(54) OPTICAL RADIATION SENSOR SYSTEM WITH CLEANING DEVICE

(75) Inventors: Gang Fang, North York (CA); John Houghton, London (CA); Yuri Lawryshyn, Komoka (CA); Joseph Lem, London (CA); Michael Sasges, London (CA); Alex Verdun, London (CA)

(73) Assignee: Trojan Technologies Inc., London (CA)

( * ) Notice: Subject to any disclaimer, the term of this patent is extended or adjusted under 35 U.S.C. 154(b) by 0 days.

(21) Appl. No.: 09/676,081

(22) Filed: Oct. 2, 2000

Related U.S. Application Data
(60) Provisional application No. 60/157,010, filed on Oct. 1, 1999.

(51) Int. Cl.[7] .............................................. G01N 21/01
(52) U.S. Cl. ....................................... 250/372; 250/435
(58) Field of Search ................................. 250/372, 435, 250/436, 438, 431; 210/748; 422/24; 436/172

(56) References Cited

U.S. PATENT DOCUMENTS

| | | | | |
|---|---|---|---|---|
| 4,482,809 A | * | 11/1984 | Maarschalkerweerd | ..... 250/436 |
| 4,622,465 A | | 11/1986 | Harig et al. | |
| 4,872,980 A | * | 10/1989 | Maarschalkerweerd | ..... 210/243 |
| 5,006,244 A | * | 4/1991 | Maarschalkerweerd | ..... 210/243 |
| 5,418,370 A | * | 5/1995 | Maarschalkerweerd | ..... 250/431 |
| 5,539,210 A | * | 7/1996 | Maarschalkerweerd | ..... 250/372 |
| 5,590,390 A | * | 12/1996 | Maarschalkerweerd | .. 422/186.3 |
| 5,964,954 A | * | 10/1999 | Matsukawa et al. | ........... 134/6 |

FOREIGN PATENT DOCUMENTS

| | | | | |
|---|---|---|---|---|
| DE | 198 12 289 A1 | 9/1999 | ............. | G01P/5/00 |
| EP | 0202891 | 11/1986 | ............. | C02F/1/32 |
| WO | WO 95 09814 A | 4/1995 | ............. | C02F/1/32 |

* cited by examiner

*Primary Examiner*—Constantine Hannaher
*Assistant Examiner*—Otilia Gabor
(74) *Attorney, Agent, or Firm*—Katten Muchin Zavis Rosenman (57) ABSTRACT

There is disclosed an optical radiation sensor system. The system includes a sensor device and a cleaning device. The sensor device detects and responds to radiation from a radiation field and includes a surface that is movable with respect to the radiation field between a first position in which the surface is in the radiation field and a second position in which at least a portion of the surface is out of the radiation field. The cleaning device operates to remove fouling materials from at least a portion of the surface in the second position. The cleaning device may be a chemical cleaning device, a mechanical cleaning device or a combined chemical/mechanical device.

35 Claims, 8 Drawing Sheets

OPTICAL RADIATION SENSOR SYSTEM WITH CLEANING DEVICE

This application claims benefit of U.S. patent application Ser. No. 60/157,010, filed Oct. 1, 1999, incorporated herein by reference.

BACKGROUND OF THE INVENTION

1. Field of the Invention

Generally, the present invention relates to an optical radiation sensor system.

2. Description of the Prior Art

Optical radiation sensors are known and find widespread use in a number of applications. One of the principal applications of optical radiation sensors is in the field of ultraviolet radiation fluid disinfection systems.

It is known that the irradiation of water with ultraviolet light will disinfect the water by inactivation of microorganisms in the water, provided the irradiance and exposure duration are above a minimum "dose" level (often measured in units of microWatt seconds per square centimetre). Ultraviolet water disinfection units such as those commercially available from Trojan Technologies Inc. under the tradenames UV700 and UV8000, employ this principle to disinfect water for human consumption. Generally, water to be disinfected passes through a pressurized stainless steel cylinder which is flooded with ultraviolet radiation. Large scale municipal waste water treatment equipment such as that commercially available from Trojan Technologies Inc. under the trade-names UV3000 and UV4000, employ the same principal to disinfect waste water. Generally, the practical applications of these treatment systems relates to submersion of treatment module or system in an open channel wherein the wastewater is exposed to radiation as it flows past the lamps. For further discussion of fluid disinfection systems employing ultraviolet radiation, see any one of the following:

U.S. Pat. No. 4,482,809,
U.S. Pat. No. 4,872,980,
U.S. Pat. No. 5,006,244,
U.S. Pat. No. 5,418,370,
U.S. Pat. No. 5,539,210, and
U.S. Pat. No. 5,590,390.

In many applications, it is desirable to monitor the level of ultraviolet radiation present within the water under treatment. In this way, it is possible to assess, on a continuous or semi-continuous basis, the level of ultraviolet radiation, and thus the overall effectiveness and efficiency of the disinfection process.

It is known in the art to monitor the ultraviolet radiation level by deploying one or more passive sensor devices near the operating lamps in specific locations and orientations which are remote from the operating lamps. These passive sensor devices may be photodiodes, photoresistors or other devices that respond to the impingent of the particular radiation wavelength or range of radiation wavelengths of interest by producing a repeatable signal level (in volts or amperes) on output leads.

Conventional ultraviolet disinfection systems often incorporate arrays of lamps immersed in a fluid to be treated. Such an arrangement poses difficulties for mounting sensors to monitor lamp output. The surrounding structure is usually a pressurized vessel or other construction not well suited for insertion of instrumentation. Simply attaching an ultraviolet radiation sensor to the lamp module can impede flow of fluid and act as attachment point for fouling and/or blockage of the ultraviolet radiation use to treat the water. Further, there is an increasing desire to utilize ultra-violet disinfection systems to treat relatively low quality water—e.g., low quality waste water from municipal waste water treatment plants. This creates a problem in that those components of the disinfection system which are in continued contact with the waste water will accumulate fouling materials. The accumulation of fouling materials on an ultra-violet radiation sensor can lead to the conveyance of misleading information to the operator about the status of the ultra-violet radiation sources. In other words, as the sensor accumulates fouling materials, its ability to sense ultra-violet radiation will be reduced. A corresponding signal would be sent to the operator who might mistake the signal for an indication that one or more of the radiation sources is not operating. Further, placing a cleaning mechanism for the sensor surface in the flow of fluid is problematic since this can impede the flow of fluid and act as an attachment point as described hereinabove.

Accordingly, it would be desirable to have an optical radiation sensor system having a surface which could be periodically cleaned while the fluid treatment system is in operation. It would be particularly advantageous if the surface of the sensor device could be cleaned in a manner which minimized or avoided impeding of the flow of fluid through the fluid treatment system.

SUMMARY OF THE INVENTION

It is an object of the present invention to provide a novel radiation source module which obviates or mitigates at least one of the above-mentioned disadvantages of the prior art.

It is another object of the present invention to provide a novel radiation source assembly which obviates or mitigates at least one of the above-mentioned disadvantages of the prior art.

Accordingly, in one of its aspects, the present invention provides an optical radiation sensor system for detecting radiation from a radiation field, the device comprising:

a sensor device for detecting and responding to radiation from the radiation field, the sensor device comprising a surface, the surface being movable with respect to the radiation field between a first position in which the surface is within the radiation field and a second position in which at least a portion of the surface is without the radiation field; and a cleaning device for removing fouling materials from at least a portion of the surface in the second position.

Thus, the present inventors have discovered an optical radiation sensor system which allows for in situ cleaning of the surface of the sensor device which receives radiation. Generally, it is preferred that the present optical radiation sensor system achieves such cleaning of the surface while the surface is being moved or has been moved with respect to the field of radiation. Many advantages accrue from this approach. First, cleaning of the surface may be achieved independently of the flow of fluid thereby avoiding leakage of cleaning agent (if used) into the flow of fluid and minimizing or obviating hydraulic head loss penalties which would result if the structural elements used to clean the surface of the sensor device were placed in the flow of fluid. Second, servicing of the sensor device is facilitated. Third, the present approach facilitates the use of mechanical cleaning, chemical cleaning or a combination of chemical/mechanical cleaning of the surface. Other advantages will become apparent to those of skill in the art.

BRIEF DESCRIPTION OF THE DRAWINGS

Embodiments of the present invention will be described with reference to the accompanying drawings, in which.

DETAILED DESCRIPTION OF THE PREFERRED EMBODIMENTS

Figure 1:
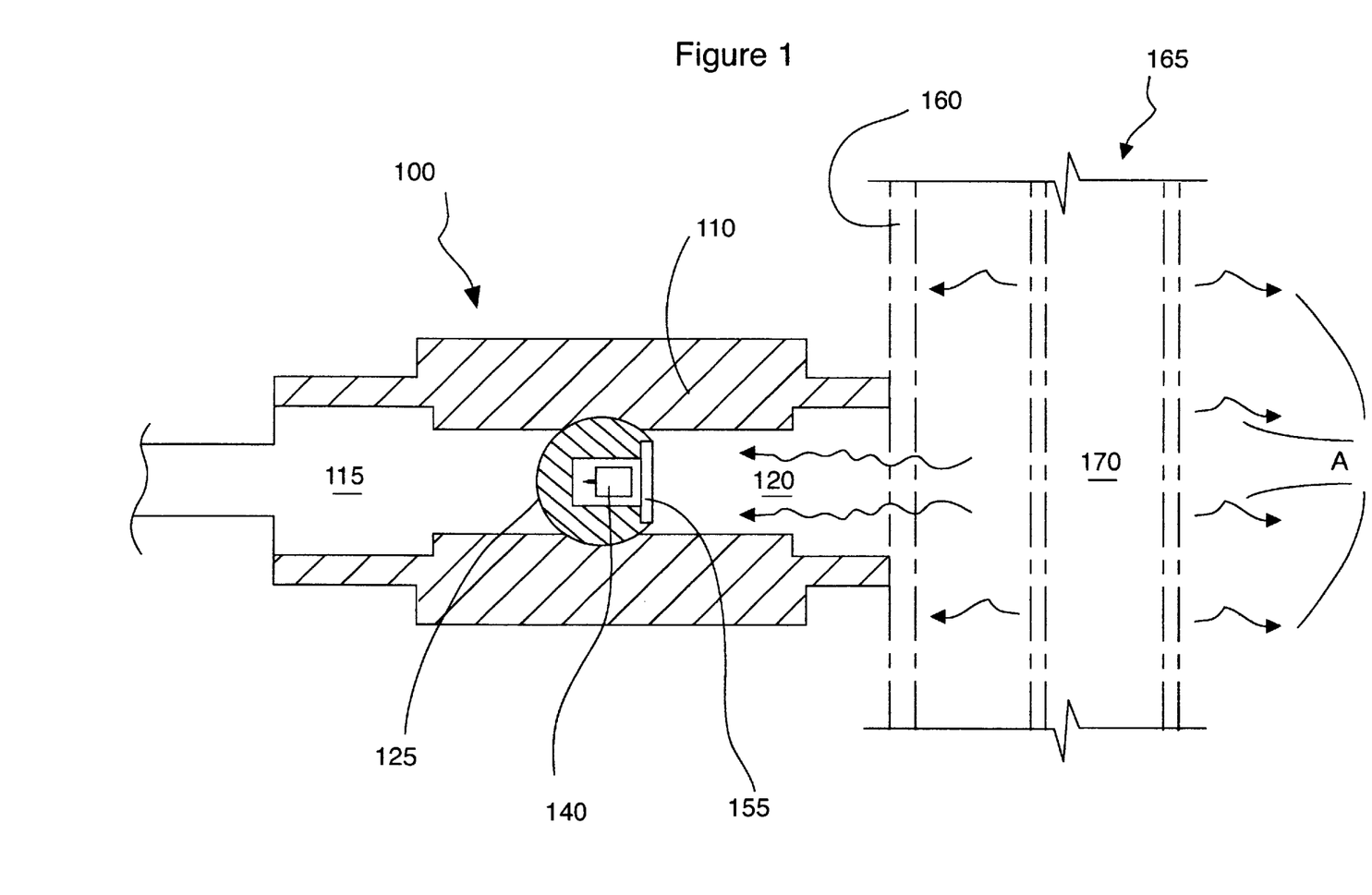
FIG. 1 illustrates a schematic of a top view of a first embodiment of the present optical radiation sensor system in a first position.
Figure 2:
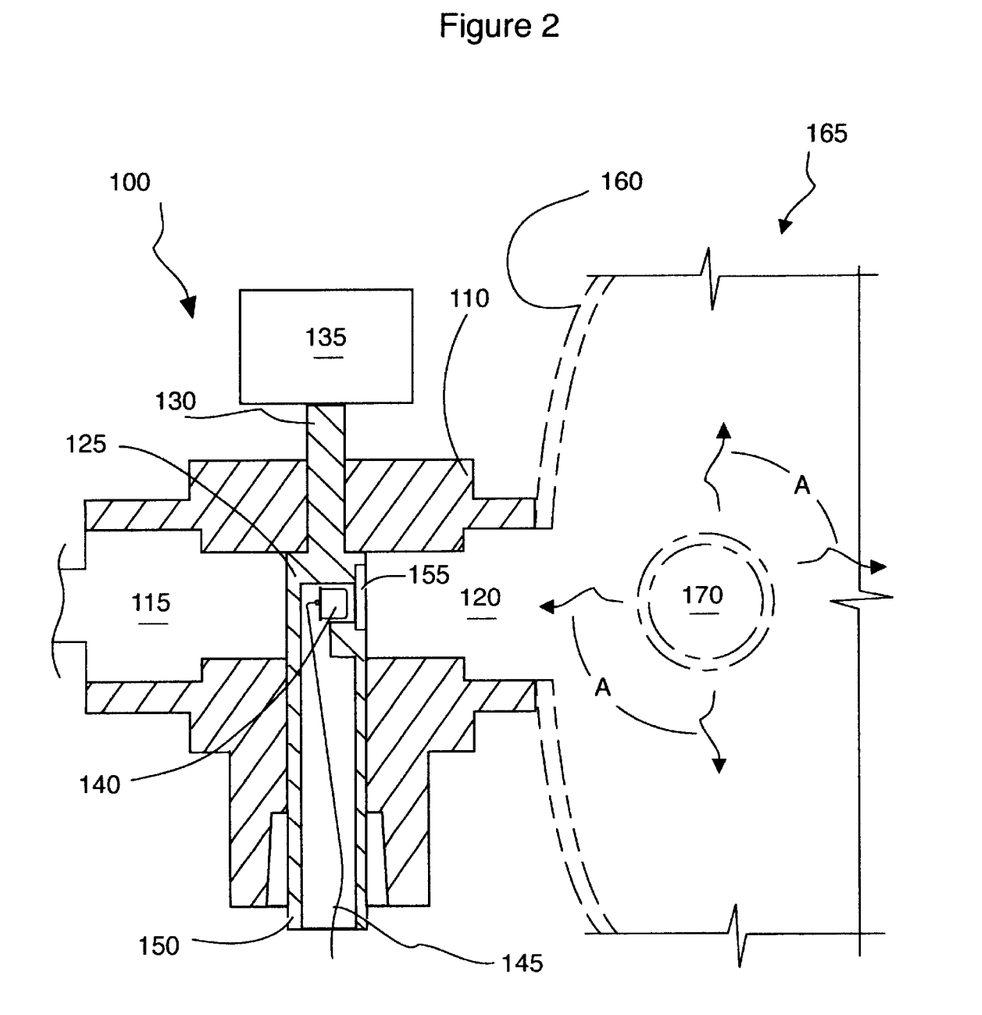
FIG. 2 illustrates a side elevation, in cross section, of the system illustrated in FIG. 1.
Figure 3:
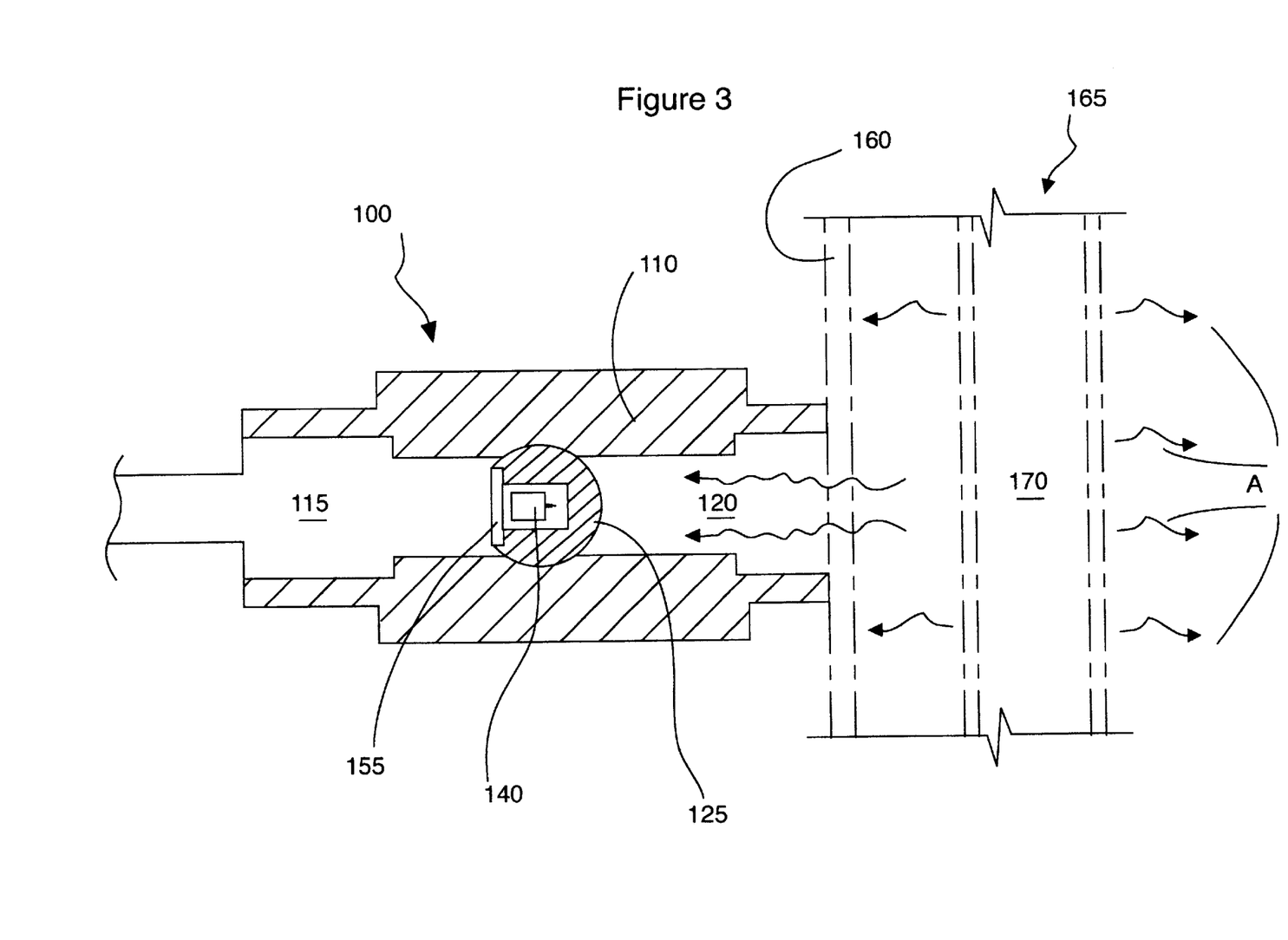
FIG. 3 illustrates a top view of the FIG. 1 embodiment in a second position.
Figure 4:
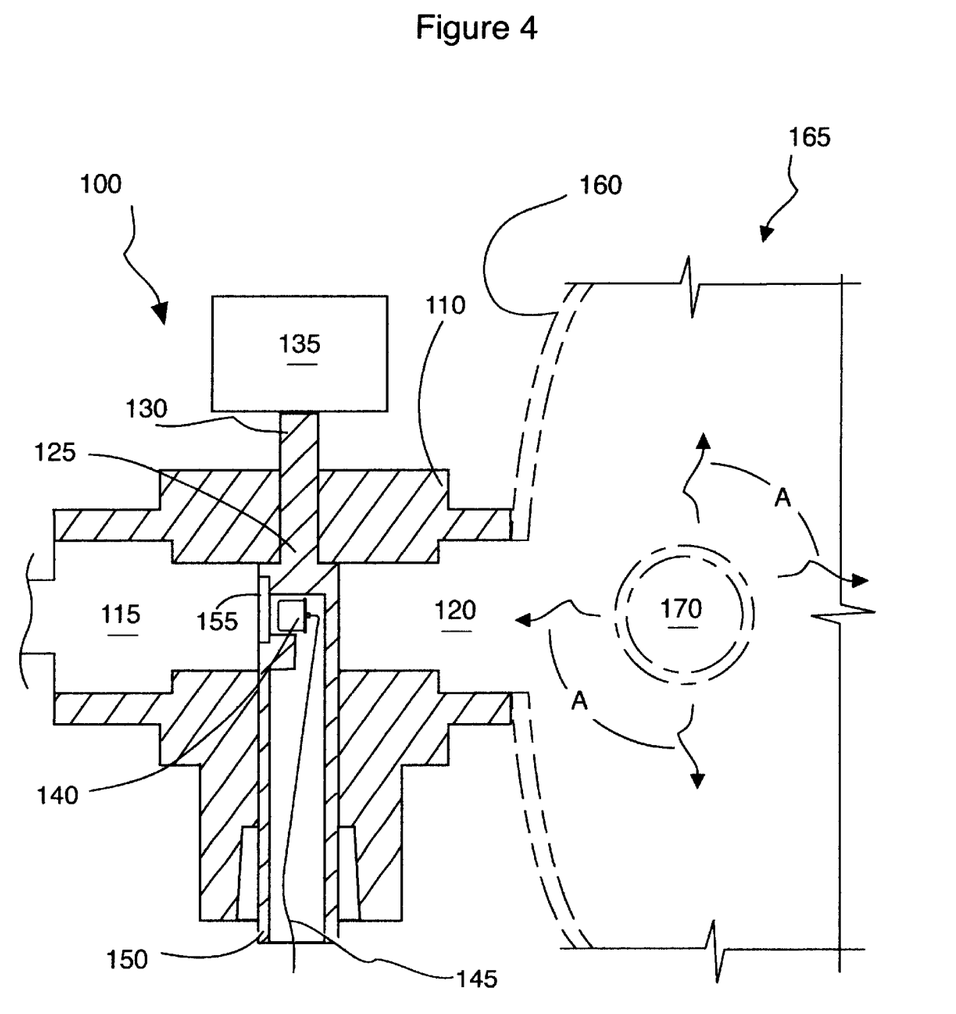
FIG. 4 illustrates a side elevation, in cross section, of FIG. 3.

FIGS. 1–4 illustrate a first embodiment of the present optical radiation sensor system. FIGS. 1 and 2 illustrate the first embodiment of the system in the first or "viewing" position, while FIGS. 3 and 4 illustrate the same embodiment in the second "cleaning" position.

Thus, with reference to FIGS. 1–4, there is illustrated an optical radiation sensor system 100 comprising a housing 110. Disposed in housing 110 is a first chamber 115 and a second chamber 120. Interposed between first chamber 115 and second chamber 120 is a sensor housing 125.

Sensor housing 125 is connected to a motor 135 via an axle 130. Disposed in sensor housing 125 is a sensor photo-diode 140. Sensor photo-diode 140 has connected to it an electrical cable 145. Preferably, sensor photo-diode is one which detects and responds to ultraviolet radiation, more preferably one which detects and responds to radiation having a wavelength in the range of from about 100 to about 400 nm, most preferably, one which detects and responds to radiation having a wavelength in the range of from about 250 to about 260 nm. Electrical cable 145 emanates out of a conduit 150 emanating from housing 110. Also disposed in sensor housing 125 is a window 155. It is preferred that window 155 form a fluid tight seal with respect to sensor housing 125. This can be achieved in a conventional manner. Further, it is preferred that window 155 be constructed from a radiation transparent material (e.g., quartz and the like).

In the illustrated embodiment, second chamber 120 of housing 110 is sealingly attached to an outer wall 160 of a fluid treatment chamber 165. Disposed within fluid treatment chamber 165 is a radiation source 170.

While not shown, attached to the distal end of first chamber 115 of housing 110 is a pressurized source of cleaning agent (e.g., acetic acid, etc.), mild inorganic acids and the like which serves to fill first chamber 115.

As will be apparent, in FIGS. 1 and 2, window 155 is adjacent to second chamber 120, whereas in FIGS. 3 and 4, window 155 is adjacent to first chamber 115.

In use, a flow of fluid (preferably water) is treated in fluid treatment chamber 165. Thus, when radiation source 170 is in use, a field of radiation is created as shown by arrows A.

As shown in FIGS. 1 and 2, a portion of the radiation from the field of radiation enters second chamber 120 and impinges on window 155. This radiation is sensed by sensor photo-diode 140 and an appropriate signal is sent to the operator about the level of radiation. The design of a control system for sensing radiation is conventional in the art as is the use thereof by an operator.

After some use, and depending on the type of fluid being treated, window 155 becomes fouled with fouling materials. When it is desired to clean window 155, motor 135 is actuated to rotate axle 130 thereby rotating sensor housing 125 to a second position as shown in FIGS. 3 and 4. In this second position, window 155 having fouling materials thereon is exposed to cleaning agent in first chamber 115. The cleaning agent serves to remove the fouling materials from window 155. The length of time for exposing window 155 to the cleaning agent in first chamber 115 can be readily determined based on historical performance of the system, the type of fluid being treated and the specific nature of the cleaning agent filling first chamber 115. Once the fouling materials have been substantially removed from window 155, motor 135 is actuated again to rotate axle 135 thereby returning window 155 to the first position illustrated in FIGS. 1 and 2 thereby putting the sensor online for detection of radiation from the radiation field.

Figure 5:
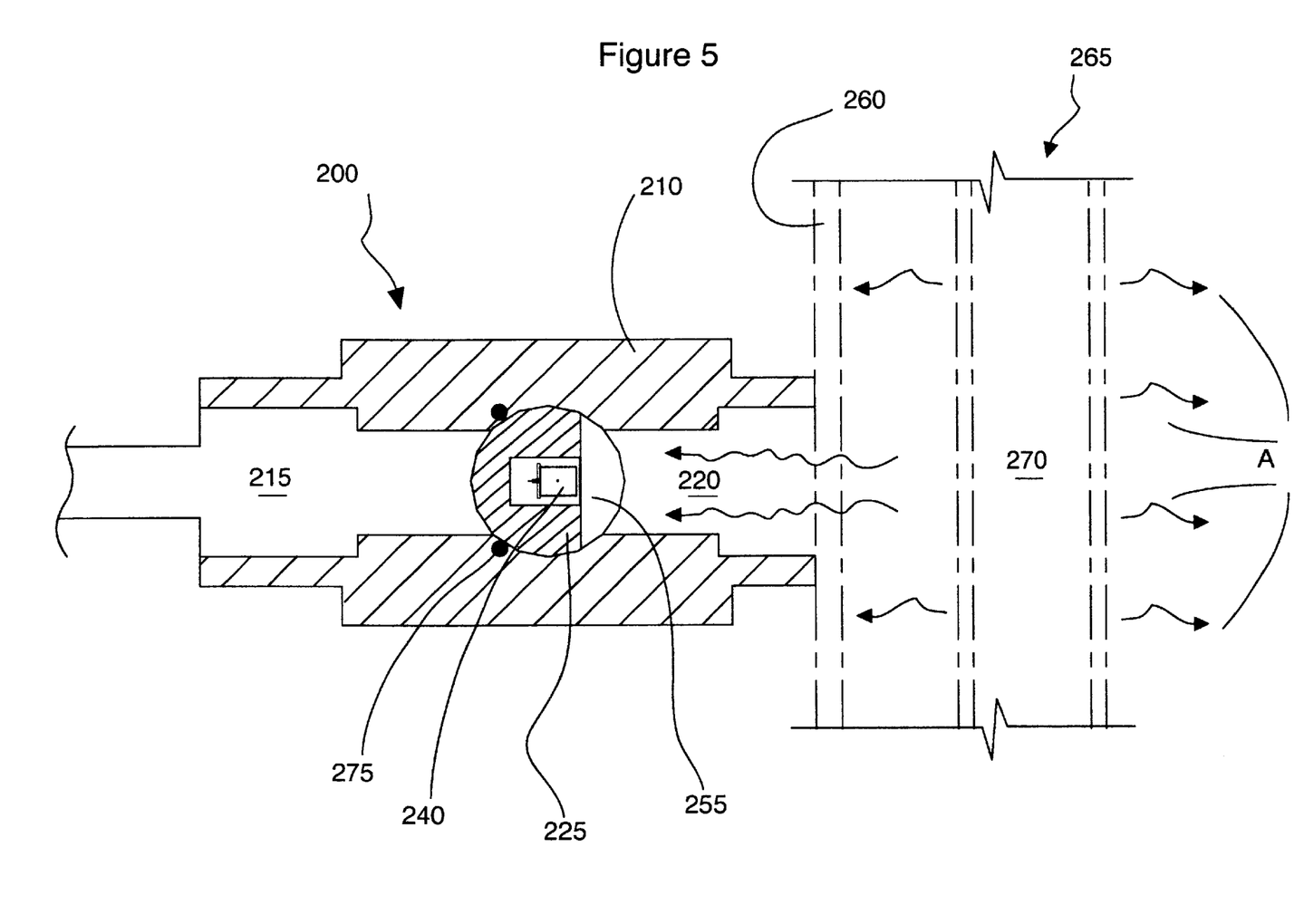
FIG. 5 illustrates a schematic of a top view of a second embodiment of the present optical radiation sensor system in a first position.
Figure 6:
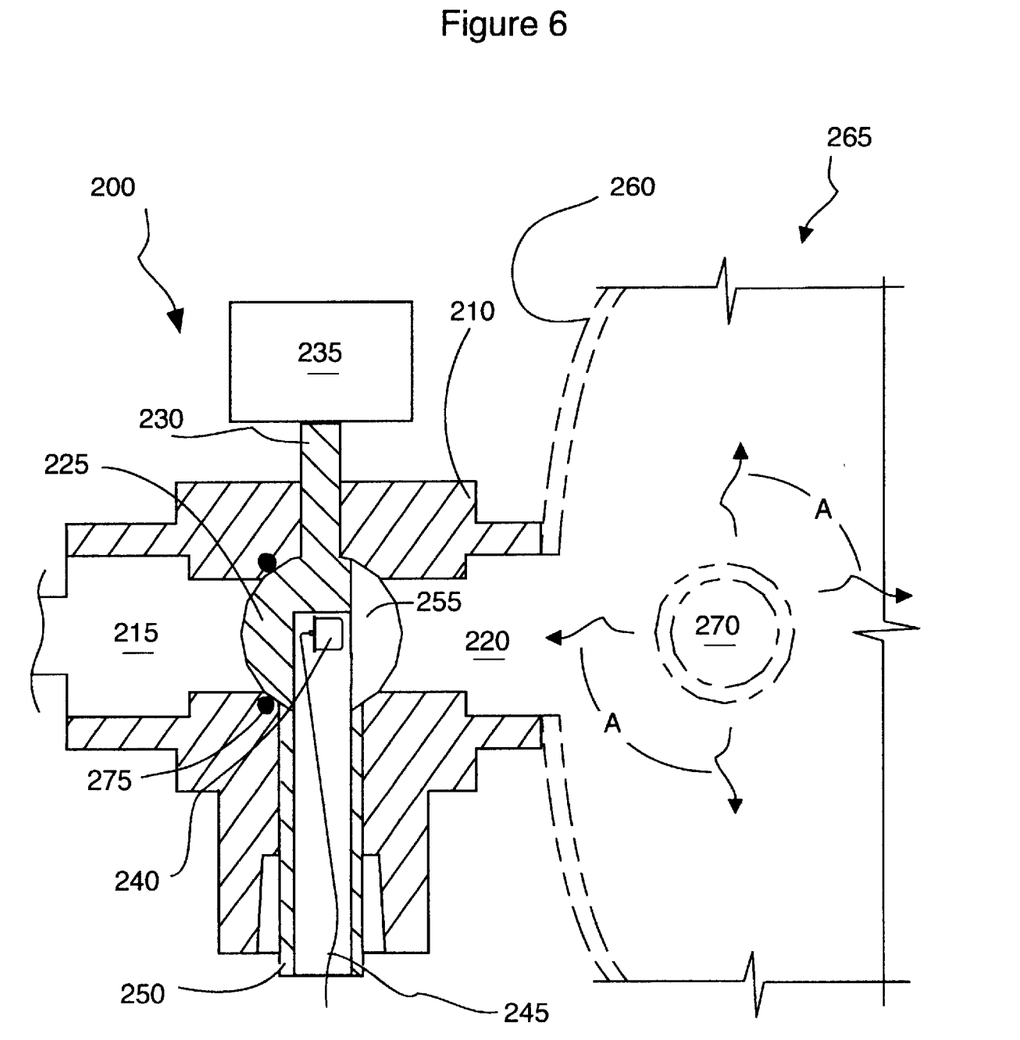
FIG. 6 illustrates a side elevation, in cross section, of the system illustrated in FIG.
Figure 7:
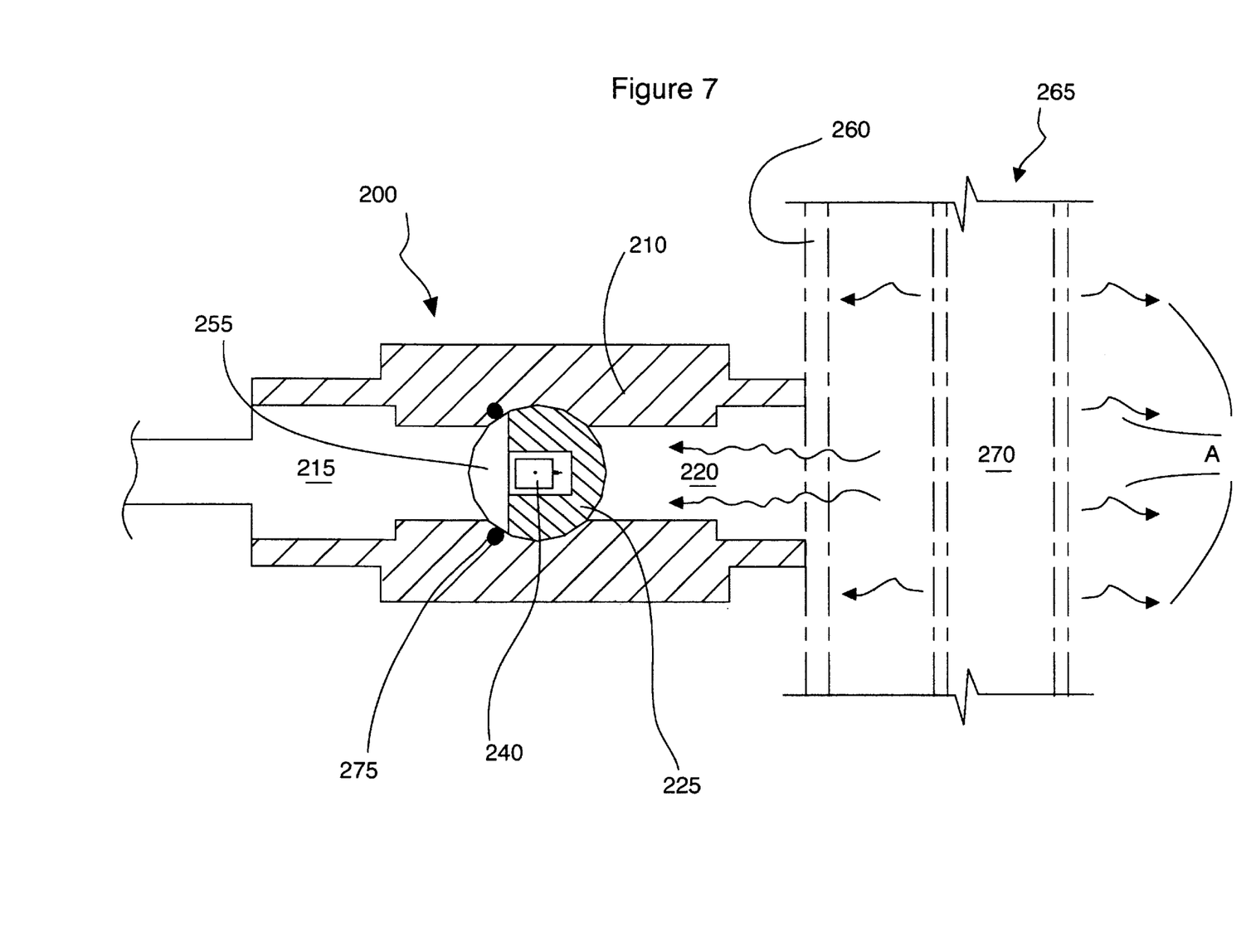
FIG. 7 illustrates a top view of the FIG. 5 embodiment in a second position.
Figure 8:
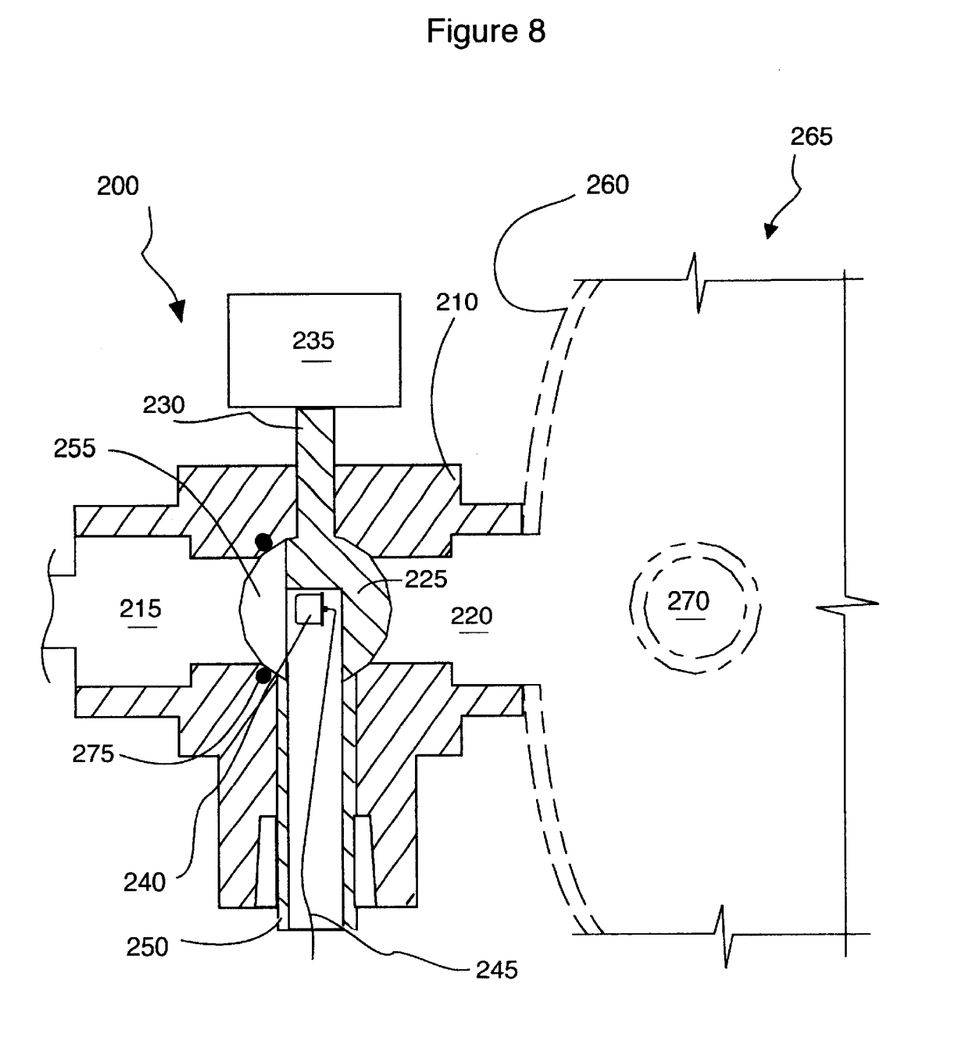
FIG. 8 illustrates a side elevation, in cross-section, of FIG. 7.

FIGS. 5–8 illustrate a second embodiment of the present optical radiation sensor system. FIGS. 5 and 6 illustrate the second embodiment of the system in the first or "viewing" position, while FIGS. 7 and 8 illustrate the same embodiment in the second or "cleaning" position.

Thus, with reference to FIGS. 5–8, there is illustrated an optical radiation sensor system 200 comprising a housing 210. Disposed in housing 210 is a first chamber 215 and a second chamber 220. Interposed between first chamber 215 and second chamber 220 is a ball housing 225.

Ball housing 225 is connected to a motor 235 via an axle 230. Disposed in ball housing 225 is a sensor photo-diode 240. Sensor photo-diode 240 has connected to it an electrical cable 245. Electrical cable 245 emanates out of a conduit 250 emanating from housing 210. Also disposed in ball housing 225 is a window 255. As shown, window 255 assumes a portion of the spherical shape of sensor housing 225. It is preferred that window 255 form a fluid tight seal with respect to ball housing 225. This can be achieved in a conventional manner. Further, it is preferred that window 255 be constructed from a radiation transparent material (e.g. quartz and the like).

In the illustrated embodiment, second chamber 220 of housing 210 is sealingly attached to an outer wall 260 of a fluid treatment chamber 265. Disposed within fluid treatment chamber 265 is a radiation source 270.

As further illustrated, disposed in housing 210 is an O-ring 275 made from a polymer material such as rubber, plastic and the like. O-ring 275 serves to create a fluid tight seal between ball housing 225 and housing 210.

As will be apparent in FIGS. 5 and 6, window 255 is adjacent to second chamber 220 whereas in FIGS. 7 and 8 window 255 is adjacent to first chamber 215.

In use, a flow of fluid (preferably water) is treated in fluid treatment chamber 265. Thus, when radiation source 270 is in use, a field of radiation is created as shown by arrows A. As shown in FIGS. 5 and 6, a portion of the radiation from the field of radiation enters second chamber 220 and impinges on window 225. This radiation is sensed by sensor photo-diode 240 and appropriate signal is sent to the operator about the level of radiation. The design of a control system for sensing radiation is conventional in the art as the use thereof by an operator.

After some use, and depending on the type of fluid being treated, window 255 becomes fouled with fouling materials. When it is desired to clean window 255, motor 235 is actuated to rotate axle 230 thereby rotating ball housing 225 to a second position as shown in FIGS. 7 and 8. As illustrated, in the second position, window 255 faces first chamber 215. During this rotation, window 255 having fouling materials thereon is wiped by O-ring 275. This interaction between window 255 and O-ring 275 results in mechanical cleaning or wiping of the fouling materials from window 255. Optionally, it is possible to combine this arrangement with the use of a chemical cleaning system as described herein above with reference to FIGS. 1–4. Once the fouling materials have been substantially removed from window 255, motor 235 is actuated to rotate axle 235 thereby returning window 255 to the first position illustrated in FIGS. 5 and 6 thereby putting the sensor on line for detection of radiation from the radiation field.

While the present invention has been described with reference to preferred and specifically illustrated embodiments, it will of course be understood by those skilled in the arts that various modifications to these preferred and illustrated embodiments may be made without the parting from the spirit and scope of the invention. For example, while the present invention has been illustrated with reference to a fluid treatment system similar in general design to the one specifically taught in U.S. Pat. No. 5,504,335 (all Figures), it is possible to employ the present radiation source assembly in a module such as the one illustrated in U.S. Pat. Nos. 5,418,370 , 5,539,210 and 5,590,390—i.e., in a fluid treatment system having an open irradiation zone in which the fluid being treated is not physically confined as it passes through the irradation zone. Further, it is possible to employ the present optical radiation sensor system in a fluid treatment which such as the one specifically taught in U.S. Pat. Nos. 5,418,370, 5,539,210 and 5,590,390—i.e., in a fluid treatment system which is a hybrid of the open and closed fluid treatment systems described above. Further a variety of cleaning devices may be used in the present optical radiation sensor system, including (without limitation): mechanical brushes, jets, cleaning agents comprising abrasive particles, cellular materials and the like. Other modifications which do not depart from the spirit and scope of the present invention will be apparent to those skilled in the art.

All publications, patents and patent applications referred to herein are incorporated by reference in their entirety to the same extent as if each individual publication, patent or patent application was specifically and individually indicated to be incorporated by reference in its entirety.

What is claimed is:

1. An optical radiation sensor for detecting radiation from a radiation field, the sensor comprising:
   a sensor device for detecting and responding to radiation from the radiation field, the sensor device comprising a surface, the surface being movable with respect to the radiation field between a first position in which the surface is within the radiation field and a second position in which at least a portion of the surface is without the radiation field; and
   a cleaning device for removing fouling materials from at least a portion of the surface in the second position.

2. The optical radiation sensor defined in claim 1, wherein the sensor device comprises a sensor element and a window which comprises the surface, the sensor element detecting and responding to radiation from the radiation field.

3. The optical radiation sensor defined in claim 2, wherein the sensor element and the window are disposed in spaced relationship with respect to one another.

4. The optical radiation sensor defined claim 2, wherein both the sensor element and the window are movable with respect to the radiation field.

5. The optical radiation sensor defined in claim 2, wherein the sensor element is fixed with respect to the radiation field and the window is movable with respect to the radiation field.

6. The optical radiation sensor defined in claim 2, wherein the window is constructed from a material which is substantially transparent to radiation.

7. The optical radiation sensor defined in claim 2, wherein the window is constructed from quartz.

8. The optical radiation sensor defined in claim 2, wherein the sensor element is disposed in a first block, the first block being movably engaged with respect to a second block.

9. The optical radiation sensor defined in claim 8, wherein the cleaning device is disposed in the first chamber.

10. The optical radiation sensor defined in claim 8, wherein the first block is connected to a motor.

11. The optical radiation sensor defined in claim 1, further comprising an actuator for causing movement between the first position and the second position.

12. The optical radiation sensor defined in claim 11, wherein the actuator comprises an electric motor.

13. The optical radiation sensor defined in claim 11, wherein the actuator comprises a hydraulic drive.

14. The optical radiation sensor defined in claim 11, wherein the actuator comprises a pneumatic drive.

15. The optical radiation sensor defined in claim 1, wherein the cleaning device comprises a mechanical cleaning device for removal of the fouling materials.

16. The optical radiation sensor defined in claim 15, wherein the cleaning device comprises a mechanical wiper which removes fouling materials from at least a portion of the surface as the surface is moved from the first position.

17. The optical radiation sensor defined in claim 16, wherein the mechanical wiper comprises a polymeric wiper.

18. The optical radiation sensor defined in claim 16, wherein the mechanical wiper comprises a brush.

19. The optical radiation sensor defined in claim 1, wherein the cleaning device comprises a chemical cleaning device for removal of the fouling materials.

20. The optical radiation sensor defined in claim 19, wherein the cleaning device comprises a first chamber for receiving the surface in the second position and a cleaning agent for removing fouling materials from the surface, the first chamber being independent of the field of radiation.

21. The optical radiation sensor defined in claim 1, wherein the cleaning device comprises a combined mechanical/chemical cleaning device for removal of the fouling materials.

22. The optical radiation sensor defined in claim 21, wherein the cleaning device comprises the combination of: (i) a mechanical wiper which removes fouling materials from at least a portion of the surface as the surface is move from the first position; and (ii) a first chamber for receiving the surface in the second position and a cleaning agent for removing fouling materials from the surface, the first chamber being independent of the field of radiation.

23. The optical radiation sensor defined in claim 22, wherein the first chamber further comprises a jet to direct cleaning agent on to the surface.

24. The optical radiation sensor defined in claim 22, wherein the first chamber is substantially sealed for receiving a pressurized supply of cleaning agent.

25. The optical radiation sensor defined in claim 1, wherein the surface of the sensor device is rotationally movable with respect to the radiation field.

26. The optical radiation sensor defined in claim 1, wherein the surface of the sensor device is translationally movable with respect to the radiation field.

27. The optical radiation sensor defined in claim 1, wherein the sensor device detects and responds to ultraviolet radiation.

28. The optical radiation sensor defined in claim 1, wherein the sensor device detects and responds to radiation having a wavelength in the range of from about 100 to about 400 nm.

29. The optical radiation sensor defined in claim 1, wherein the sensor device detects and responds to radiation having a wavelength in the range of from about 240 to about 300 nm.

30. A fluid treatment system for treating a flow of fluid, the system comprising the optical radiation sensor system defined in claim 1.

31. The fluid treatment system defined in claim 30, comprising a fluid irradiation zone having disposed therein at least one radiation source.

32. The fluid treatment system defined in claim 31, wherein the fluid irradiation zone is disposed in open channel for receiving the flow of fluid.

33. The fluid treatment system defined in claim 31, wherein the fluid irradiation zone comprises a closed cross-section for confining the flow of fluid.

34. The fluid treatment system defined in claim 31, wherein the at least one radiation source comprises a longitudinal axis disposed substantially parallel to the direction of flow fluid in the fluid irradiation zone.

35. The fluid treatment system defined in claim 31, wherein the at least one radiation source comprises a longitudinal axis disposed substantially transverse to the direction of flow fluid in the fluid irradiation zone.

* * * * *